United States Patent
Martin et al.

(10) Patent No.: US 7,714,936 B1
(45) Date of Patent: *May 11, 2010

(54) OMNIVIEW MOTIONLESS CAMERA ORIENTATION SYSTEM

(75) Inventors: H. Lee Martin, Knoxville, TN (US); Daniel P. Kuban, Oak Ridge, TN (US); Steven D. Zimmermann, Knoxville, TN (US); Nicholas Busko, Knoxville, TN (US)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/887,319

(22) Filed: Jul. 2, 1997
(Under 37 CFR 1.47)

Related U.S. Application Data

(63) Continuation of application No. 08/386,912, filed on Feb. 8, 1995, now abandoned, and a continuation of application No. 08/339,663, filed on Nov. 11, 1994, now abandoned, which is a continuation of application No. 08/189,585, filed on Jan. 31, 1994, now Pat. No. 5,384,588, which is a continuation-in-part of application No. 08/014,508, filed on Feb. 8, 1993, now Pat. No. 5,359,363, which is a continuation-in-part of application No. 07/699,366, filed on May 13, 1991, now Pat. No. 5,185,667.

(51) Int. Cl.
*H04N 9/64* (2006.01)
*H04N 5/30* (2006.01)

(52) U.S. Cl. .......................... 348/576; 348/36; 348/39; 348/207.99; 382/282; 382/293

(58) Field of Classification Search .................. 348/15, 348/36, 143, 207, 17, 147, 207.1, 580; 359/718, 359/364, 363; 382/293–298, 282, 154, 43, 382/41; 395/137–139; *H04N 5/30*
See application file for complete search history.

(56) References Cited

U.S. PATENT DOCUMENTS 3,723,805 A    3/1973   Scarpino et al. ........ 315/27 GD (Continued)

FOREIGN PATENT DOCUMENTS

| EP | 0011909 A1 | 6/1980 |
| EP | 0 971 540 B1 | 6/2002 |
| JP | 2-127877 | 5/1990 |
| WO | WO 82/03712 | 10/1982 |

OTHER PUBLICATIONS

English Abstract 2-127877 (A), May 16, 1990, for "Electronic Still Camera Provided With Fisheye Lens" for Japanese Application No. 63-281550.

(Continued)

*Primary Examiner*—M. Lee
(74) *Attorney, Agent, or Firm*—Finnegan, Henderson, Farabow, Garrett & Dunner LLP

(57) ABSTRACT

An apparatus and method is provided for converting digital images for use in an imaging system. The apparatus includes a data memory which stores digital data representing an image having a circular or spherical field of view such as an image captured by a fish-eye lens, a control input for receiving a signal for selecting a portion of the image, and a converter responsive to the control input for converting digital data corresponding to the selected portion into digital data representing a planar image for subsequent display. Various methods include the steps of storing digital data representing an image having a circular or spherical field of view, selecting a portion of the image, and converting the stored digital data corresponding to the selected portion into digital data representing a planar image for subsequent display. In various embodiments, the data converter and data conversion step may use an orthogonal set of transformation algorithms.

1 Claim, 6 Drawing Sheets

U.S. PATENT DOCUMENTS

| | | | | |
|---|---|---|---|---|
| 4,125,862 | A | 11/1978 | Catano | 358/140 |
| 4,152,724 | A | 5/1979 | Hunter | 358/109 |
| 4,191,967 | A | 3/1980 | Dansac et al. | 358/113 |
| 4,463,380 | A | 7/1984 | Hooks, Jr. | 358/160 |
| 4,518,898 | A | 5/1985 | Tarnowski et al. | 315/371 |
| 4,549,208 | A | 10/1985 | Kamejima et al. | 358/108 |
| 4,661,855 | A | 4/1987 | Gülck | 358/225 |
| 4,670,648 | A | 6/1987 | Hall et al. | 250/216 |
| 4,728,839 | A | 3/1988 | Coughlan et al. | 310/112 |
| 4,736,436 | A * | 4/1988 | Yasukawa et al. | 382/16 |
| 4,751,660 | A | 6/1988 | Hedley | 364/518 |
| 4,772,942 | A | 9/1988 | Tuck | 358/87 |
| 4,797,942 | A | 1/1989 | Burt | 382/41 |
| 4,807,158 | A | 2/1989 | Blanton et al. | 395/125 |
| 4,835,532 | A | 5/1989 | Fant | 340/728 |
| 4,858,002 | A | 8/1989 | Zobel | 358/98 |
| 4,858,149 | A | 8/1989 | Quarendon | 364/522 |
| 4,899,293 | A | 2/1990 | Dawson et al. | 364/521 |
| 4,918,473 | A | 4/1990 | Blackshear | 354/81 |
| 4,924,094 | A | 5/1990 | Moore | 250/334 |
| 4,945,367 | A | 7/1990 | Blackshear | 354/81 |
| 4,965,844 | A | 10/1990 | Oka et al. | 382/44 |
| 4,991,020 | A | 2/1991 | Zwirn | 358/160 |
| 5,005,083 | A | 4/1991 | Grage et al. | 358/181 |
| 5,020,114 | A | 5/1991 | Fujioka et al. | 382/44 |
| 5,023,725 | A | 6/1991 | McCutchen | 358/231 |
| 5,048,102 | A | 9/1991 | Tararine et al. | 382/41 |
| 5,063,604 | A * | 11/1991 | Weiman | 382/170 |
| 5,067,019 | A | 11/1991 | Juday et al. | 358/160 |
| 5,068,735 | A | 11/1991 | Tuchiya et al. | 358/209 |
| 5,077,609 | A | 12/1991 | Manelphe | 358/109 |
| 5,173,948 | A | 12/1992 | Blackham et al. | 382/44 |
| 5,175,808 | A | 12/1992 | Sayre | 395/133 |
| 5,185,667 | A * | 2/1993 | Zimmermann | 348/207.99 |
| 5,200,818 | A | 4/1993 | Neta et al. | 358/87 |
| 5,231,673 | A | 7/1993 | Elenga | 382/6 |
| 5,313,306 | A * | 5/1994 | Kuban et al. | 348/65 |
| 5,359,363 | A * | 10/1994 | Kuban et al. | 348/36 |
| 5,384,588 | A * | 1/1995 | Martin et al. | 348/14.1 |
| 5,396,583 | A | 3/1995 | Chen et al. | 397/127 |
| 5,796,426 | A | 8/1998 | Gullichsen et al. | |
| RE36,207 | E * | 5/1999 | Zimmermann et al. | 348/207.99 |
| 7,382,399 | B1 * | 6/2008 | McCall et al. | 348/207.99 |

OTHER PUBLICATIONS

"Fooling the Eye", Suzanne Oliver, Forbes, Jan. 16, 1995 (p. 94).

G. David Ripley, "DVI—A Digital Multimedia Technology", Communications of the ACM Jul. 1989 vol. 32, No. 7, pp. 811-822.

M. Onoe et al., "Digital Processing of Images Taken by Fish-Eye Lens", IEEE: Proceedings, New York, 1982, vol. 1, p. 105-8.

N. Greene, "Environment Mapping and Other Applications of World Projections", IEEE Computer Graphics and Applications, Nov. 1986, pp. 21-29.

N. Greene, "A Method of Modeling Sky for Computer Animations", Proc. First Int'l. Conf. Engineering and Computer Graphics, Aug. 1984, pp. 297-300.

J. Blinn et al., "Texture and Reflection in Computer Generated Images," Comm. ACM, vol. 19, No. 10, 1976, pp. 542-547.

N. Greene et al., "Creating Raster Omnimax Images from Multiple Perspective Views Using the Elliptical Weighted Average Filter", IEEE Computer Graphics and Applications, Jun. 1986, pp. 21-27.

R. Kingslake, "Optical System Design", Academic Press, 1983, pp. 86-87.

S. Ray, "The Lens in Action", Hastings House, 1976, pp. 114-117.

F. Pearson II, "Map Projections Theory and Applications", CRC Press, Inc., 1990, pp. 215-345.

A. Paeth, "Digital Cartography for Computer Graphics", Graphics Gems, 1990, pp. 307-320.

G. Wolberg, "Digital Image Warping", IEEE Computer Society Press, 1988.

F. Kenton Musgrave, "A Panoramic Virtual Screen for Ray Tracing", Graphics Gems, 1992, pp. 288-294.

J. D. Foley et al., "Computer Graphics: Principles and Practice", 1990, 1996, pp. 229-381.

Intel Corporation, "Action Media 750 Production Tool Reference", 1988, 1991.

S. Morris, "Digital Video Interactive—A New Integrated Format for Multi-Media Information", Microcomputer for Information Management, Dec. 1987, 4(4):249-261.

"Declaration of Scott Gilbert in Support of Defendant Infinite Pictures' Memorandum in Opposition to Plaintiff's Motion for Preliminary Injunction", *Omniview, Inc.* v. *Infinite Pictures, Inc.*, Civ. Action No. 3-96-849.

Heckbert, "Fundamentals of Texture Mapping and Image Warping", Report No. UCB/CSD 89/516, Jun. 1989.

Heckbert, "The PMAT and Poly User's Manual", NYIT Document, 1983.

Video Tape—*IPIX* v. *Infinite Pictures*, Ref. No. 01096.58642, Exhibit Nos. 216 and 217.

Data Sheets for Imaging Products, Defendant's Exhibit 202, pp. 40-63.

Data Sheets for TMC2301, TMC2302, Defendant's Exhibit 402, 1 sheet.

Data Sheets for Simplified Block Diagram, Plaintiff's Exhibit 409, pp. 41-77.

Robert Kingslake, Optical System Design, Academic Press, pp. 86-87, 1983.

Exhibit 4—"The Omnigraph, Omnidirectional Spherical Photography" and "Omnigraphics, second report," Richard J. Felix, 1970's.

Exhibits 6, 26, 29, 30, 32-35—Omnigraphics course materials, California State University—Richard J. Felix—1974 to 1994.

Exhibit 17—"Multiplex Video Display", Richard J. Felix, Feb. 7, 1994.

Protest under rule 37 C.F.R. §1.291(a) in U.S. Appl. No. 08/662,410.

Supplement to Protest under rule 37 C.F.R. §1.291(a) in U.S. Appl. No. 08/662,410.

* cited by examiner

OMNIVIEW MOTIONLESS CAMERA ORIENTATION SYSTEM

This application is a continuation of application Ser. No. 08/386,912, filed Feb. 8, 1995 now abandoned.

This application is a continuation of U.S. application Ser. No. 08/339,663 filed Nov. 11, 1994 now abandoned, which is a continuation of U.S. application Ser. No. 08/189,585 filed Jan. 31, 1994 (now U.S. Pat. No. 5,384,588), which is a continuation-in-part of U.S. application Ser. No. 08/014,508 filed Feb. 8, 1993 (now U.S. Pat. No. 5,359,363), which is a continuation-in-part of U.S. application Ser. No. 07/699,366 filed May 13, 1991 (now U.S. Pat. No. 5,185,667). Each of the above-referenced U.S. patents is expressly incorporated by reference herein.

This invention was made with Government support under contract NAS1-18855 awarded by NASA. The Government has certain rights in this invention.

BACKGROUND OF THE INVENTION

1. Technical Field

This invention relates generally to an apparatus and method for transforming perspective-distorted circular field of view images into non-distorted, normal perspective images having various orientations, rotations, and magnifications within the field of view.

2. Related Information

Camera viewing systems are used in abundance for surveillance, inspection, security, and remote sensing. Remote viewing is critical, for example, for robotic manipulation tasks. Close viewing is necessary for detailed manipulation tasks wile wide-angle viewing aids positioning of the robotic system to avoid collisions with the work space. Most of these systems use either a fixed-mount camera with a limited viewing field to reduce distortion, or they utilize mechanical pan-and-tilt platforms and mechanized zoom lenses to orient the camera and magnify its image. In the applications where orientation of the camera and magnification of its image are required, the mechanical solution is large in size and can subtend a significant volume making the viewing system difficult to conceal or use in close quarters. Several cameras are usually necessary to provide wide-angle viewing of the work space.

In order to provide a maximum amount of viewing coverage or subtended angle, mechanical pan/tilt mechanisms usually use motorized drives and gear mechanisms to manipulate the vertical and horizontal orientation. An example of such a device is shown in U.S. Pat. No. 4,728,839 issued to J. B. Coughlan, et al, on Mar. 1, 1988. Collisions with the working environment caused by these mechanical pan/tilt orientation mechanisms can damage both the camera and the work space and impede the remote handling operation. Simultaneously, viewing in said remote environments is extremely important to the performance of inspection and manipulation activities.

Camera viewing systems that use internal optics to provide wide viewing angles have also been developed in order to minimize the size and volume of the camera and the intrusion into the viewing area. These systems rely on the movement of either a mirror or prism to change the tilt-angle of orientation and provide mechanical rotation of the entire camera to change the pan angle of orientation. Additional lenses are used to minimize distortion. Using this means, the size of the camera orientation system can be minimized, but "blind spots" in the center of the view result. Also, these systems typically have no means of magnifying the image and or producing multiple images from a single camera.

References that may be relevant to the evaluation of the present invention are U.S. Pat. Nos. 4,772,942 issued to M. J. Tuck on Sep. 20, 1988; 5,023,725 issued to D. McCutchen on Jun. 11, 1991; 5,067,019 issued to R. D. Juday on Nov. 19, 1991; and 5,068,735 issued to K. Tuchiya, et al on Nov. 26, 1991.

Accordingly, it is an object of the present invention to provide an apparatus that can provide an image of any portion of the viewing space within a selected field-of-view without moving the apparatus, and then electronically correct for visual distortions of the view.

It is another object of the present invention to provide horizontal orientation (pan), vertical orientation (tilt) and rotational orientation (rotation) of the viewing direction with no moving mechanisms.

It is another object of the present invention to provide the ability to magnify or scale the image (zoom in and out) electronically.

It is another object of the present invention to provide electronic control of the image intensity (iris level).

It is another object of the present invention to be able to accomplish pan, tilt, zoom, rotation, and iris adjustments with simple inputs made by a lay person from a joystick, keyboard controller, or computer controlled means.

It is also an object of the present invention to provide accurate control of the absolute viewing direction and orientations using said input devices.

A further object of the present invention is to provide the ability to produce multiple images with different orientations and magnifications simultaneously from a single input image.

Another object of the present invention is to be able to provide these images at real-time video rates, e.g. thirty transformed images per second, and to support various display format standards such as the National Television Standards Committee RS-170 signal format and/or higher resolution formats currently under development.

It is also an object of the present invention to provide a system that can be used for automatic or manual surveillance of selected environments, with optical views of these environments corrected electronically to remove distortion so as to facilitate this surveillance.

These and other objects of the present invention will become apparent upon consideration of the drawings hereinafter in combination with a complete description thereof.

DISCLOSURE OF THE INVENTION

In accordance with the present invention, there is provided an omnidirectional viewing system that produces the equivalent of pan, tilt, zoom, and rotation within a selected field-of-view with no moving parts. Further, the present invention includes means for controlling this omnidirectional viewing in surveillance applications. This device includes a means for digitizing an incoming or prerecorded video image signal, transforming a portion of the video image based upon operator or preselected commands, and producing one or more output images that are in correct perspective for human viewing. In one embodiment, the incoming image is produced by a fisheye lens which has a wide angle field-of-view. This image is captured into an electronic memory buffer. A portion of the captured image, either in real time or as prerecorded, containing a region-of-interest is transformed into a perspective correct image by an image processing computer. The image processing computer provides direct mapping of the image region-of-interest into a corrected image using an orthogonal set of transformation algorithms. The viewing orientation is designated by a command signal generated by either a human operator or computerized input. The transformed image is deposited in a second electronic memory buffer where it is then manipulated to produce the output image or images as requested by the command signal. This is coupled with appropriate alarms and command outputs to provide a complete surveillance system for selected environments.

BEST MODE FOR CARRYING OUT THE INVENTION

In order to minimize the size of the camera orientation system while maintaining the ability to zoom, a camera orientation system that utilizes electronic image transformations rather than mechanisms was developed. While numerous patents on mechanical pan-and-tilt systems have been filed, no approach using strictly electronic transforms and wide angle optics is known to have been successfully implemented. In addition, the electro-optical approach utilized in the present invention allows multiple images to be extracted from the output of a single camera. These images can be then utilized to energize appropriate alarms, for example, as a specific application of the basic image transformation in connection with a surveillance system. As utilized herein, the term "surveillance" has a wide range including, but not limited to, determining ingress or egress from a selected environment. Further, the term "wide angle" as used herein means a field-of-view of about eighty degrees or greater. Motivation for this device came from viewing system requirements in remote handling applications where the operating envelop of the equipment is a significant constraint to task accomplishment.

Figure 1:
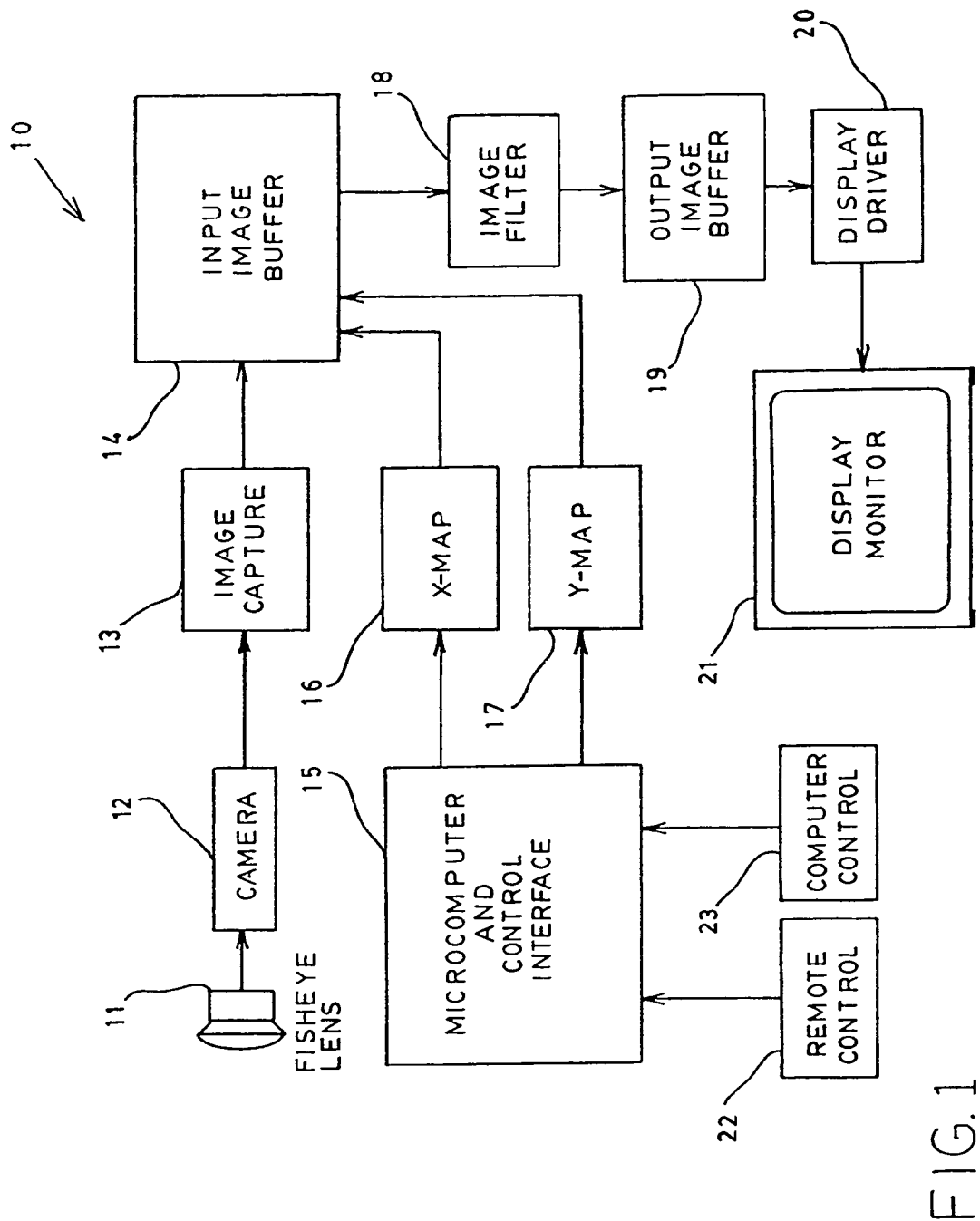
FIG. 1 shows a schematic block diagram of the signal processing portion of the present invention illustrating the major components thereof.

The principles of the optical transform utilized in the present invention can be understood by reference to the system 10 of FIG. 1. (This is also set forth in the afore-cited U.S. patent application Ser. No. 07/699,366 that is incorporated herein by reference.) Shown schematically at 11 is a wide angle, e.g., a fisheye, lens that provides an image of the environment with a 180 degree field-of-view. The lens is attached to a camera 12 which converts the optical image into an electrical signal. These signals are then digitized electronically 13 and stored in an image buffer 14 within the present invention. An image processing system consisting of an X-MAP and a Y-MAP processor shown as 16 and 17, respectively, performs the two-dimensional transform mapping. The image transform processors are controlled by the microcomputer and control interface 15. The microcomputer control interface provides initialization and transform parameter calculation for the system. The control interface also determines the desired transformation coefficients based on orientation angle, magnification, rotation, and light sensitivity input from an input means such as a joystick controller 22 or computer input means 23. The transformed image is filtered by a 2-dimensional convolution filter 18 and the output of the filtered image is stored in an output image buffer 19. The output image buffer 19 is scanned out by display electronics 20 to a video display device 21 for viewing.

A range of lens types can be accommodated to support various fields of view. The lens optics 11 correspond directly with the mathematical coefficients used with the X-MAP and Y-MAP processors 16 and 17 to transform the image. The capability to pan and tilt the output image remains even though a different maximum field of view is provided with a different lens element.

The invention can be realized by proper combination of a number of optical and electronic devices. The lens 11 is exemplified by any of a series of wide angle lenses from, for example, Nikon, particularly the 8 mm F2.8. Any video source 12 and image capturing device 13 that converts the optical image into electronic memory can serve as the input for the invention such as a Videk Digital Camera interfaced with Texas Instrument's TMS 34061 integrated circuits. Input and output image buffers 14 and 19 can be constructed using Texas Instrument TMS44C251 video random access memory chips or their equivalents. The control interface can be accomplished with any of a number of microcontrollers including the Intel 80C196. The X-MAP and Y-MAP transform processors 16 and 17 and image filtering 19 can be accomplished with application specific integrated circuits or other means as will be known to persons skilled in the art. The display driver can also be accomplished with integrated circuits such as the Texas Instruments TMS34061. The output video signal can be of the NTSC RS-170, for example, compatible with most commercial television displays in the United States. Remote control 22 and computer control 23 are accomplished via readily available switches and/or computer systems that also will be well known. These components function as a system to select a portion of the input image (fisheye or other wide angle) and then mathematically transform the image to provide the proper prospective for output. The keys to the success of the invention include:

(1) the entire input image need not be transformed, only the portion of interest;

(2) the required mathematical transform is predictable based on the lens characteristics; and 3) calibration coefficients can be modified by the end user to correct for any lens/camera combination supporting both new and retrofit applications.

Figure 3:
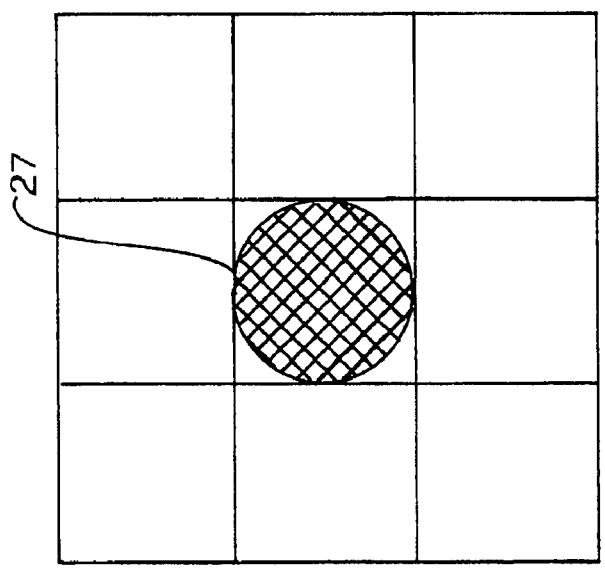
FIG. 3 is an exemplary drawing of the output image after correction for a desired image orientation and magnification within the original image.
Figure 2:
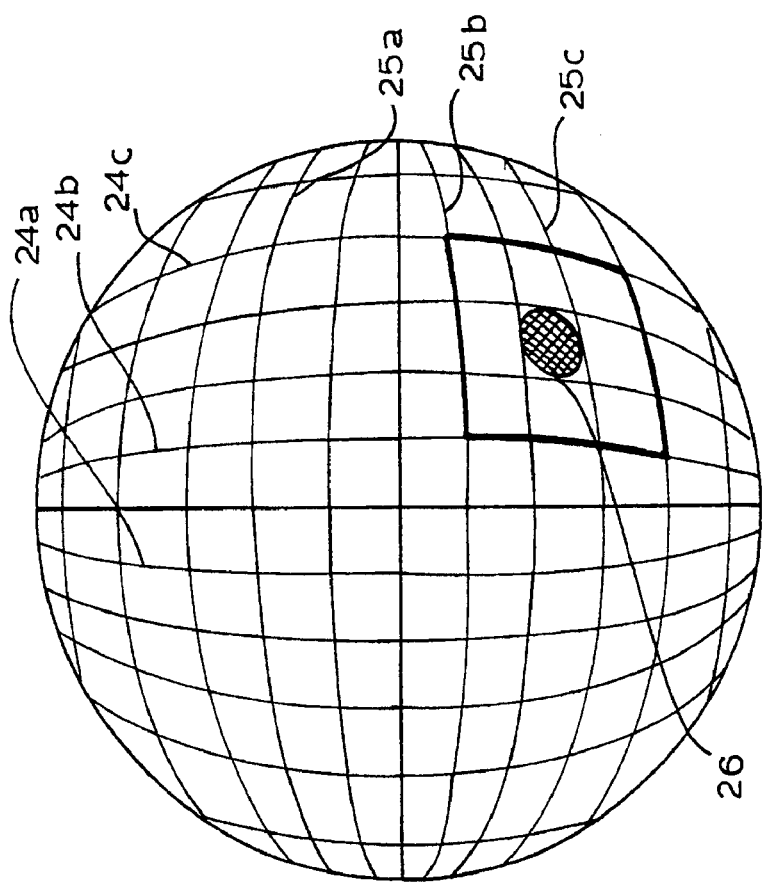
FIG. 2 is an exemplary drawing of a typical fisheye image used as input by the present invention. Lenses having other field-of-view values will produce images with similar distortion, particularly when the field-of-view is about eighty degrees or greater.

The transformation that occurs between the input memory buffer 14 and the output memory buffer 19, as controlled by the two coordinated transformation circuits 16 and 17, is better understood by referring to FIGS. 2 and 3. The image shown in FIG. 2 is a rendering of the image of a grid pattern produced by a fisheye lens. This image has a field-of-view of 180 degrees and shows the contents of the environment throughout an entire hemisphere. Notice that the resulting image in FIG. 2 is significantly distorted relative to human perception. Similar distortion will be obtained even with lesser field-of-view lenses. Vertical grid lines in the environment appear in the image plane as 24a, 24b, and 24c. Horizontal grid lines in the environment appear in the image plane as 25a, 25b, and 25c. The image of an object is exemplified by 26. A portion of the image in FIG. 2 has been corrected, magnified, and rotated to produce the image shown in FIG. 3. Item 27 shows the corrected representation of the object in the output display. The results shown in the image in FIG. 3 can be produced from any portion of the image of FIG. 2 using the present invention. The corrected perspective of the view is demonstrated by the straightening of the grid pattern displayed in FIG. 3. In the present invention, these transformations can be performed at real-time video rates (e.g., thirty times per second), compatible with commercial video standards.

The transformation portion of the invention as described has the capability to pan and tilt the output image through the entire field of view of the lens element by changing the input means, e.g. the joystick or computer, to the controller. This allows a large area to be scanned for information as can be useful in security and surveillance applications. The image can also be rotated through any portion of 360 degrees on its axis changing the perceived vertical of the displayed image. This capability provides the ability to align the vertical image with the gravity vector to maintain a proper perspective in the image display regardless of the pan or tilt angle of the image. The invention also supports modifications in the magnification used to display the output image. This is commensurate with a zoom function that allows a change in the field of view of the output image. This function is extremely useful for inspection and surveillance operations. The magnitude of zoom provided is a function of the resolution of the input camera, the resolution of the output display, the clarity of the output display, and the amount of picture element (pixel) averaging that is used in a given display. The invention supports all of these functions to provide capabilities associated with traditional mechanical pan (through 180 degrees), tilt (through 180 degrees), rotation (through 360 degrees), and zoom devices. The digital system also supports image intensity scaling that emulates the functionality of a mechanical iris by shifting the intensity of the displayed image based on commands from the user or an external computer.

The postulates and equations that follow are based on the image transformation portion of the present invention utilizing a wide angle lens as the optical element. These also apply to other field-of-view lens systems. There are two basic properties and two basic postulates that describe the perfect wide angle lens system. The first property of such a lens is that the lens has a $2\pi$ steradian field-of-view and the image it produces is a circle. The second property is that all objects in the field-of-view are in focus, i.e. the perfect wide angle lens has an infinite depth-of-field. The two important postulates of this lens system (refer to FIGS. 4 and 5) are stated as follows:

Postulate 1: Azimuth Angle Invariability

For object points that lie in a content plane that is perpendicular to the image plane and passes through the image plane origin, all such points are mapped as image points onto the line of intersection between the image plane and the content plane, i.e. along a radial line. The azimuth angle of the image points is therefore invariant to elevation and object distance changes within the content plane.

Postulate 2: Equidistant Projection Rule

The radial distance, r, from the image plane origin along the azimuth angle containing the projection of the object point is linearly proportional to the zenith angle $\beta$, where $\beta$ is defined as the angle between a perpendicular line through the image plane origin and the line from the image plane origin to the object point. Thus the relationship:

$$r = k\beta \qquad (1)$$

Figure 4:
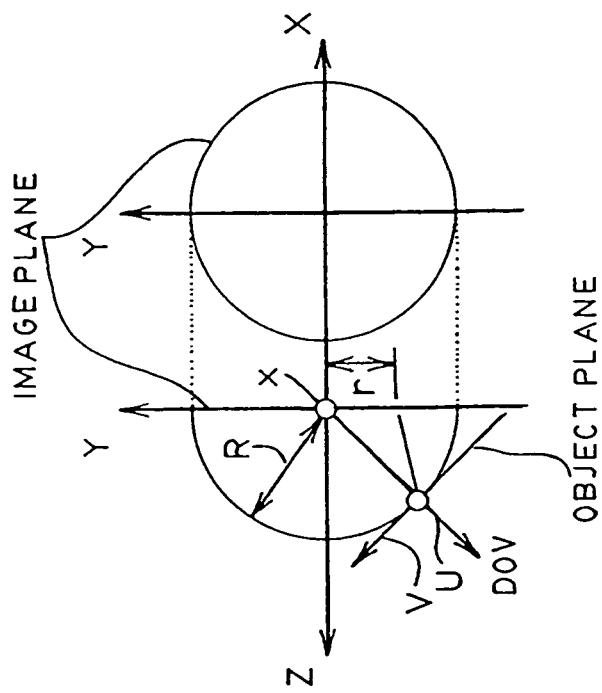
FIG. 4 is a schematic diagram of the fundamental geometry that the present invention embodies to accomplish the image transformation.

Using these properties and postulates as the foundation of the lens system, the mathematical transformation for obtaining a perspective corrected image can be determined. FIG. 4 shows the coordinate reference frames for the object plane and the image plane. The coordinates u,v describe object points within the object plane. The coordinates x,y,z describe points within the image coordinate frame of reference.

The object plane shown in FIG. 4 is a typical region of interest to determine the mapping relationship onto the image plane to properly correct the object. The direction of view vector, DOV[x,y,z], determines the zenith and azimuth angles for mapping the object plane, UV, onto the image plane, XY. The object plane is defined to be perpendicular to the vector, DOV[x,y,z].

The location of the origin of the object plane in terms of the image plane [x,y,z] in spherical coordinates is given by:

$$x = D \sin \beta \cos \partial$$

$$y = D \sin \beta \sin \partial$$

$$z = D \cos \beta \qquad (2)$$

where D=scaler length from the image plane origin to the object plane origin, $\beta$ is the zenith angle, and $\partial$ is the azimuth angle in image plane spherical coordinates. The origin of object plane is represented as a vector using the components given in Equation 1 as:

$$DOV[x,y,z] = [D \sin \beta \cos \partial, D \sin \beta \sin \partial, D \cos \beta] \qquad (3)$$

DOV[x,y,z] is perpendicular to the object plane and its scaler magnitude D provides the distance to the object plane. By aligning the YZ plane with the direction of action of DOV[x,y,z], the azimuth angle $\partial$ becomes either 90 or 270 degrees and therefore the x component becomes zero resulting in the DOV[x,y,z] coordinates:

$$DOV[x,y,z] = [0, -D \sin \beta, D \cos \beta] \qquad (4)$$

Figure 5:
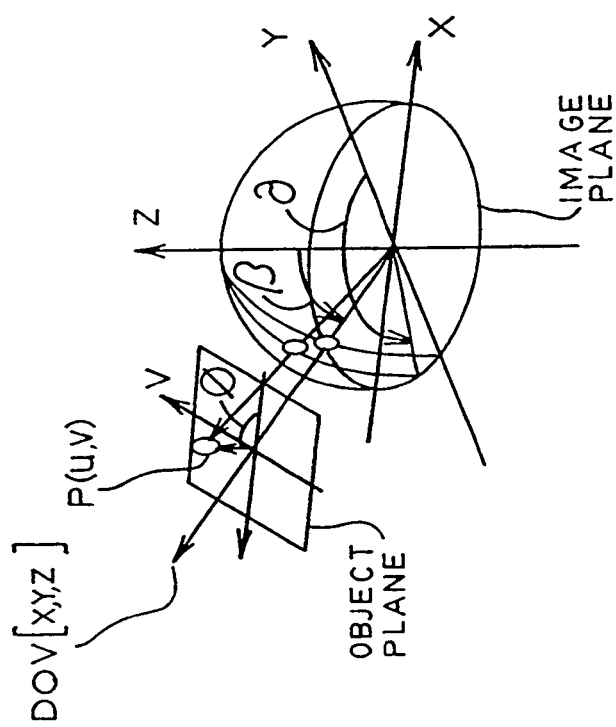
FIG. 5 is a schematic diagram demonstrating the projection of the object plane and position vector into image plane coordinates.

Referring now to FIG. 5, the object point relative to the UV plane origin in coordinates relative to the origin of the image plane is given by the following:

$$x = u$$

$$y = v \cos \beta$$

$$z = v \sin \beta \qquad (5)$$

therefore, the coordinates of a point P(u,v) that lies in the object plane can be represented as a vector P[x,y,z] in image plane coordinates:

$$P[x,y,z] = [u, v \cos \beta, v \sin \beta] \qquad (6)$$

where P[x,y,z] describes the position of the object point in image coordinates relative to the origin of the UV plane. The object vector O[x,y,z] that describes the object point in image coordinates is then given by:

$$O[x,y,z] = DOV[x,y,z] + P[x,y,z] \qquad (7)$$

$$O[x,y,z] = [u, v \cos \beta - D \sin \beta, v \sin \beta + D \cos \beta] \qquad (8)$$

Projection onto a hemisphere of radius R attached to the image plane is determined by scaling the object vector O[x, y,z] to produce a surface vector S[x,y,z]:

$$S[x, y, z] = \frac{RO[x, y, z]}{|O[x, y, z]|} \quad (9)$$

By substituting for the components of O[x,y,z] from Equation 8, the vector S[x,y,z] describing the image point mapping onto the hemisphere becomes:

$$S[x, y, z] = \frac{RO[u, (v\cos\beta - D\sin\beta), (v\sin\beta + D\cos\beta)]}{\sqrt{u^2 + (v\cos\beta - D\sin\beta)^2 + (v\sin\beta + D\cos\beta)^2}} \quad (10)$$

The denominator in Equation 10 represents the length or absolute value of the vector O[x,y,z] and can be simplified through algebraic and trigonometric manipulation to give:

$$S[x, y, z] = \frac{RO[u, (v\cos\beta - D\sin\beta), (v\sin\beta + D\cos\beta)]}{\sqrt{u^2 + v^2 + D^2}} \quad (11)$$

From Equation 11, the mapping onto the two-dimensional image plane can be obtained for both x and y as:

$$x = \frac{Ru}{\sqrt{u^2 + v^2 + D^2}} \quad (12)$$

$$y = \frac{R(v\cos\beta - D\sin\beta)}{\sqrt{u^2 + v^2 + D^2}} \quad (13)$$

Additionally, the image plane center to object plane distance D can be represented in terms of the image circular radius R by the relation:

$$D = mR \quad (14)$$

where m represents the scale factor in radial units R from the image plane origin to the object plane origin. Substituting Equation 14 into Equations 12 and 13 provides a means for obtaining an effective scaling operation or magnification which can be used to provide zoom operation.

$$x = \frac{Ru}{\sqrt{u^2 + v^2 + m^2 R^2}} \quad (15)$$

$$y = \frac{R(v\cos\beta - mR\sin\beta)}{\sqrt{u^2 + v^2 + m^2 R^2}} \quad (16)$$

Using the equations for two-dimensional rotation of axes for both the UV object plane and the XY image plane the last two equations can be further manipulated to provide a more general set of equations that provides for rotation within the image plane and rotation within the object plane.

$$x = \frac{R[uA - vB + mR\sin\beta\sin\partial]}{\sqrt{u^2 + v^2 + m^2 R^2}} \quad (17)$$

-continued $$y = \frac{R[uC - vD - mR\sin\beta\cos\partial]}{\sqrt{u^2 + v^2 + m^2 R^2}} \quad (18)$$

where:

$A = (\cos\emptyset \cos\partial - \sin\emptyset \sin\partial \cos\beta)$ $B = (\sin\emptyset \cos\partial + \cos\emptyset \sin\partial \cos\beta)$ $C = (\cos\emptyset \sin\partial + \sin\emptyset \cos\partial \cos\beta)$ $D = (\sin\emptyset \sin\partial - \cos\emptyset \cos\partial \cos\beta) \quad (19)$ and where:
R=radius of the image circle
β=zenith angle
∂=Azimuth angle in image plane
Ø=Object plane rotation angle
m=Magnification
u,v=object plane coordinates
x,y=image plane coordinates The Equations 17 and 18 provide a direct mapping from the UV space to the XY image space and are the fundamental mathematical result that supports the functioning of the present omnidirectional viewing system with no moving parts. By knowing the desired zenith, azimuth, and object plane rotation angles and the magnification, the locations of x and y in the imaging array can be determined. This approach provides a means to transform an image from the input video buffer to the output video buffer exactly. Also, the image system is completely symmetrical about the zenith, therefore, the vector assignments and resulting signs of various components can be chosen differently depending on the desired orientation of the object plane with respect to the image plane. In addition, these postulates and mathematical equations can be modified for various lens elements as necessary for the desired field-of-view coverage in a given application.

The input means defines the zenith angle, β, the azimuth angle, ∂, the object rotation, Ø, and the magnification, m. These values are substituted into Equations 19 to determine values for substitution into Equations 17 and 18. The image circle radius, R, is a fixed value that is determined by the camera lens and element relationship. The variables u and v vary throughout the object plane determining the values for x and y in the image plane coordinates.

From the foregoing, it can be seen that a wide angle lens provides a substantially hemispherical view that is captured by a camera. The image is then transformed into a corrected image at a desired pan, tilt, magnification, rotation, and focus based on the desired view as described by a control input. The image is then output to a television display with the perspective corrected. Accordingly, no mechanical devices are required to attain this extensive analysis and presentation of the view of an environment through 180 degrees of pan, 180 degrees of tilt, 360 degrees of rotation, and various degrees of zoom magnification.

As indicated above, one application for the perspective correction of images obtained with a motionless wide angle camera is in the field of surveillance. The term "surveillance" is meant to include inspection and like operations as well. It is often desired to continuously or periodically view a selected environment to determine activity in that environment. The term "environment" is meant to include such areas as rooms, warehouses, parks and the like. This activity might be, for example, ingress or egress of some object relative to that environment. It might also be some action that is taking place in that environment. It may be desired to carry out this surveillance either automatically at the desired frequency (or continuously), or upon demand by an operator. The size of the environment may require more than one motionless camera for complete surveillance.

Figure 6:
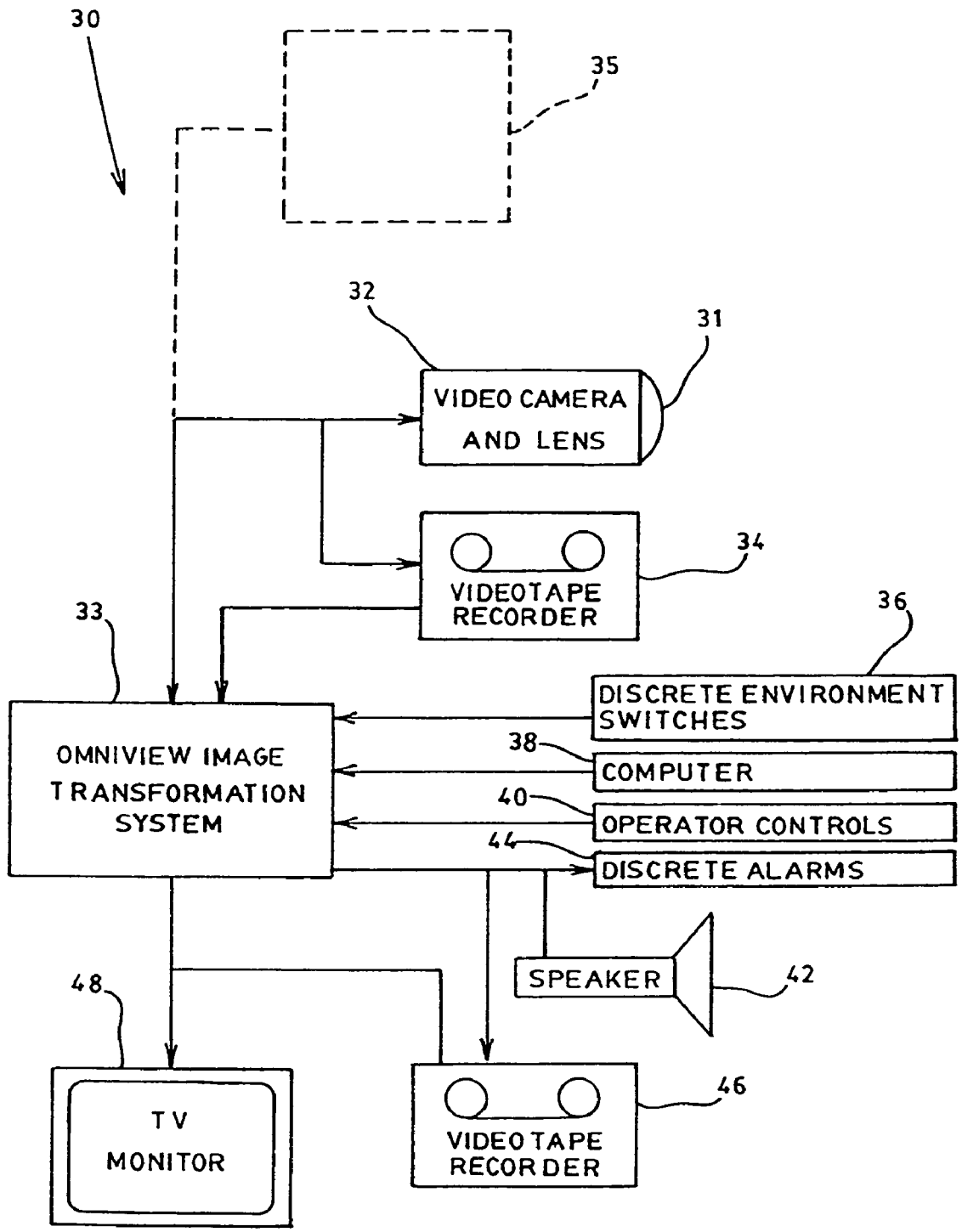
FIG. 6 is a block diagram of the present invention as utilized for surveillance/inspection applications incorporating the basic transformation of video images obtained with, for example, wide angle lenses to correct for optical distortions due to the lenses, together with the control of the surveillance/inspection and appropriate alarm systems.

Such a surveillance system is indicated generally at 30 of FIG. 6. A video camera unit 32, including a wide angle lens 31, is utilized to view the selected environment (or portion of the environment), with the output therefrom being electrical signals related to the elements as seen by the camera system. These signals, when present, are either directly presented to an image transformation system 33 (the components of FIG. 1 without the camera/lens and the TV monitor thereof) or to a videotape recorder 34 for subsequent processing in the image transformation system 33. This permits evaluation during "post event" review as well as a review of events that occur in real time. It will be understood that additional camera-lens units in an environment, as well as videotape recorders, can be utilized as indicated at 35.

Various external elements are utilized to govern the operation of the transformation system. For example, appropriate discrete switches 36 are used for the selection of the environment or portion of the environment to be monitored. These switches can be positioned (and operated) either at the control center or at the environment (or other remote location). When positioned in the environment, these switches can indicate some action occurring in the environment (door opening, window breaking, etc.) with the result that the virtual camera of the system is directed to the point of interest and then signal an external alarm for creating an audible alarm if desired. Also, alarm conditions can activate the video tape recorder discussed below. Since the system monitors the presence of an incoming video signal, the device can signal an alarm when the incoming video signal is disrupted. Where the monitoring is to be preselected, one input can be a computer 38. Another form of control is through the use of operator controls 40 such that the operator can select at any time the operation of the transformation. Options that are available in either of these types of control are "Quad display" (either through the control by the computer 38 or the operator controls 40) wherein four displays occur on a monitor. Another option available through either control is that of "tweening" which is a selection of moving the effective view of the camera incrementally between active points or switching between active cameras within the environment. As previously described, these inputs are used also for selecting pan, tilt, zoom and rotation.

The output of the transformation system 33 is typically in digital format. As such, this output can control alarm enunciators 42 positioned at any location, or other forms of discrete alarms 44. They can also activate a videotape recording machine 46. In addition, the alarms 44 can be used to detect and announce loss of video signal, and permit external interrogation (manual or automated) of system status by the computer interface of the system parameters including component or power failure. Such interrogation would include verification of operation, video input, pan-tilt-rotation angles, magnification and setup parameters. As in the system of FIG. 1, this surveillance system 30 provides for pictorial environment display on a TV-type monitor 48 and/or on the tape of the recording machine 46.

Figure 7A:
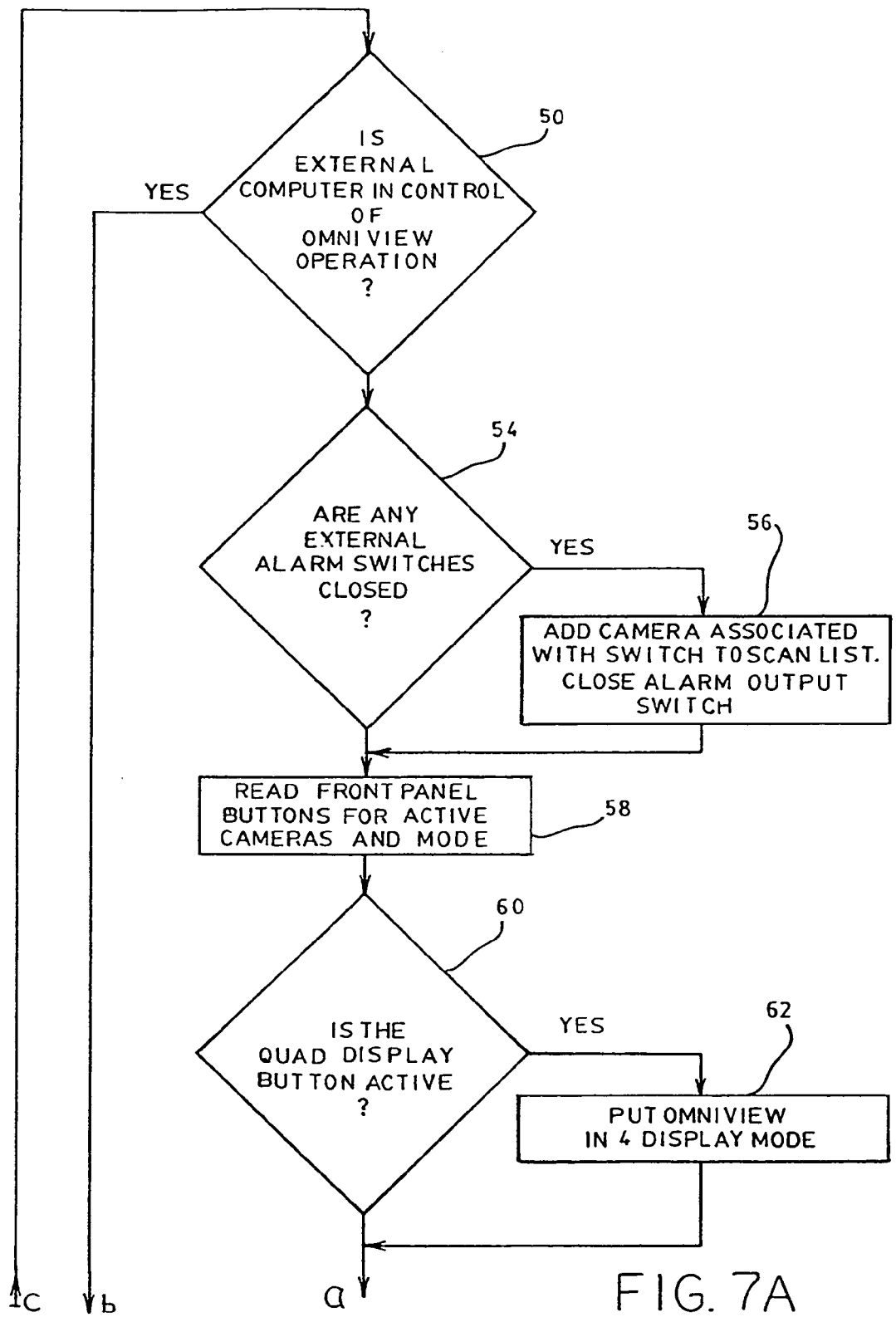
FIGS. 7A and 7B, together, show a logic flow diagram illustrating one specific embodiment of controller operation for manual and automatic surveillance operations of the present invention.
Figure 7B:
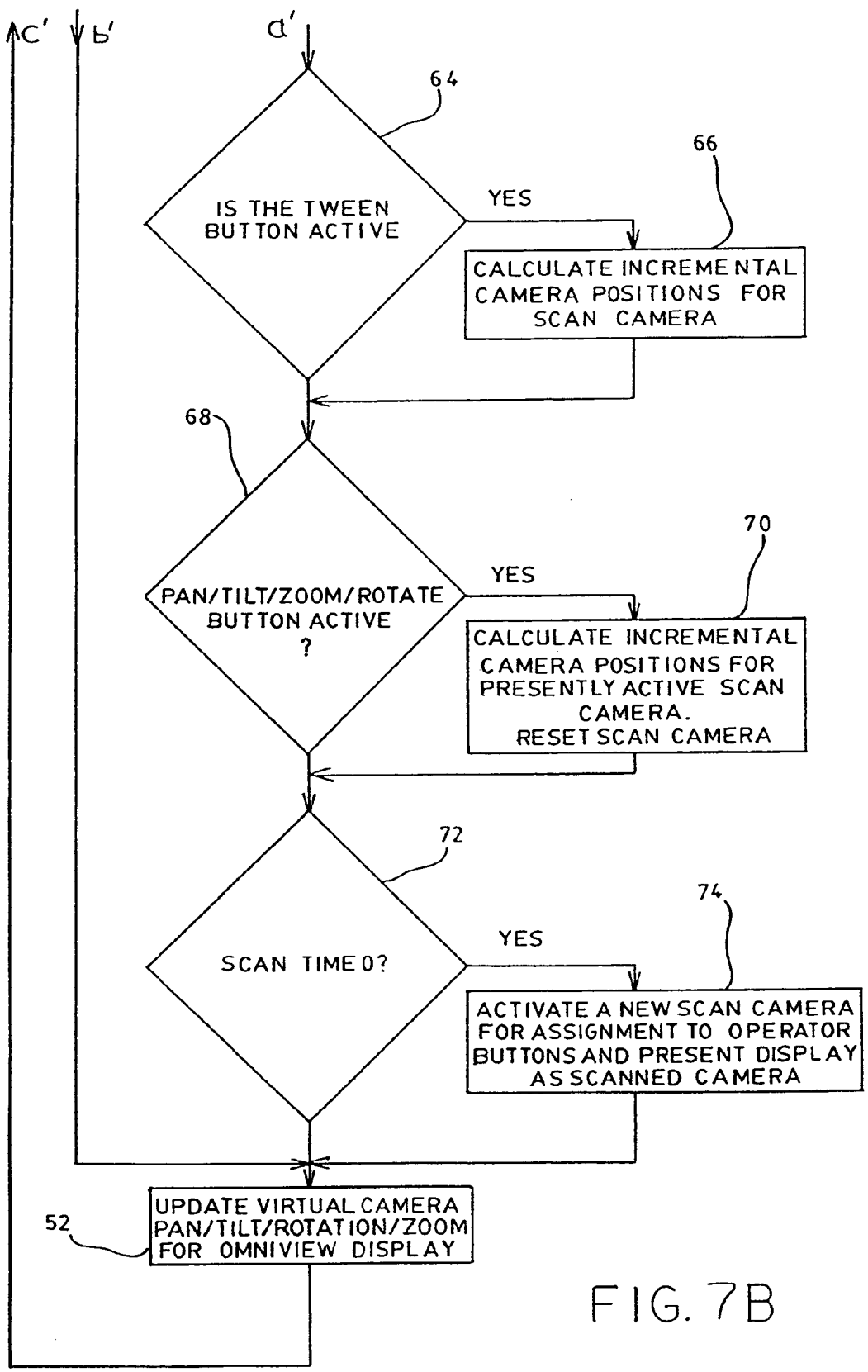

FIGS. 7A and 7A, jointly, form a logic flow diagram that illustrates how one specific embodiment of the controller 30 can perform manual and automatic surveillance activities. A decision is made at 50 as to whether the system is under computer (external) control (see 38 of FIG. 6) or manual (internal) control. If under computer operation, the camera orientations and magnifications are communicated directly to the system for action at 52. In the event of internal control, it is next determined if any environmental switches are closed as at 54. These switches typically are hard wired, magnetic infrared or other forms that indicate a change in the environment in a certain location. The choice of a specific type of switch for each application will be known by persons skilled in the art. These changes (if "YES") give rise to signals at 56 to point its visual camera in the direction of interest and then signal an external alarm for creating an audible alarm 42 and/or turning on the video tape recorder 34.

After initiating these steps, or if the answer is "NO" at 54, the switches on the unit's control panel are read at 58 to determine the configuration and display actions needed. "Quad display" (either four displays or one display on the monitor 48) is checked at 60 and, if the four displays are desired (the "YES"), this is initiated at 62. If "tweening" (incremental effective movement of a camera or switching between cameras) is desired, this is checked at 64 and the appropriate selection is made at 66.

Inputs for pan, tilt, zoom and rotation are interpreted at 68 and applied to the presently active display camera. Every user interaction resets the scan timer at 70 so that while the user is in control, no virtual camera change is occurring. When the scan time reaches zero, as monitored at 72, the next camera is made active and the image being displayed changes direction and/or content as at 74 to thereby update operation as at 52.

From the foregoing, it will be understood by those versed in the art that an advanced surveillance system has been provided. This system utilizes at least one motionless video camera, having a wide angle lens, within the environment where surveillance is desired. The perspective of images obtained with the lens/camera are corrected through transformation according to the technology of Ser. No. 07/699,366 either directly or after storage in a videotape recorder. Many operational conditions are selectable including tilt, pan, zoom and rotation. Further, multi-image displays can be obtained, and the images can be incrementally scanned or switching between cameras are other options. The system provides for automatic operation coupled with user operation if desired.

While certain specific elements of construction are indicated throughout the description of the present invention, these are given for illustration and not for limitation. Thus, the invention is to be limited only by the appended claims and their equivalents.

The invention claimed is:

1. A memory for a signal processor, comprising:

a data structure, responsive to a control input representing a selection of a portion of an image stored in said memory, wherein said selection is chosen across a field of view, said data structure representing an orthogonal set of transformation algorithms; and a buffer memory adapted to store digital image data for transformation;

wherein said data structure transforms data according to the following equations:

$$X = \frac{R[uA - vB + mR\sin\beta\sin\vartheta]}{\sqrt{(u^2 + v^2 + m^2R^2)}}$$

$$Y = \frac{R[uC - vD - mR\sin\beta\cos\vartheta]}{\sqrt{(u^2 + v^2 + m^2R^2)}}$$

where:

$A = (\cos\theta \cos\partial - \sin\theta \sin\partial \cos\beta)$ $B = (\sin\theta \cos\partial + \cos\theta \sin\partial \cos\beta)$ $C = (\cos\theta \sin\partial + \sin\theta \cos\partial \cos\beta)$ $D = (\sin\theta \sin\partial - \cos\theta \cos\partial \cos\beta)$ and where:
R=radius of the image circle
$\beta$=zenith angle
$\partial$=Azimuth angle in image plane
$\theta$=object plane rotation angle
m=Magnification
u,v=object plane coordinates
x,y=image plane coordinates.

* * * * *